(12) United States Patent
Coulon et al.

(10) Patent No.: US 11,020,008 B2
(45) Date of Patent: Jun. 1, 2021

(54) METHOD AND SYSTEM FOR ACQUIRING AND ANALYZING PHYSIOLOGICAL DATA

(71) Applicant: @HEALTH, Aix en Provence (FR)

(72) Inventors: David Coulon, Aix en Provence (FR); Jean-Michel Tarlet, Trets (FR)

(73) Assignee: @HEALTH, Aix en Provence (FR)

( * ) Notice: Subject to any disclaimer, the term of this patent is extended or adjusted under 35 U.S.C. 154(b) by 0 days.

(21) Appl. No.: 15/777,429

(22) PCT Filed: Nov. 16, 2016

(86) PCT No.: PCT/FR2016/052973
§ 371 (c)(1),
(2) Date: May 18, 2018

(87) PCT Pub. No.: WO2017/085403
PCT Pub. Date: May 26, 2017

(65) Prior Publication Data
US 2018/0333058 A1 Nov. 22, 2018

(30) Foreign Application Priority Data
Nov. 19, 2015 (FR) .................................. 15 02422

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0006* (2013.01); *A61B 5/0022* (2013.01);
(Continued)

(58) Field of Classification Search
CPC ..... A61B 5/0205; A61B 5/0022; A61B 5/085; A61B 5/0402; A61B 5/08; A61B 5/747;
(Continued)

(56) References Cited

U.S. PATENT DOCUMENTS

2004/0228217 A1 11/2004 Szeto
2007/0265538 A1 11/2007 Badilini
(Continued)

OTHER PUBLICATIONS

International Search Report (PCT/ISA/210) dated Mar. 9, 2017, by the European Patent Office as the International Searching Authority for International Application No. PCT/FR2016/052973.

*Primary Examiner* — Catherine M Voorhees
(74) *Attorney, Agent, or Firm* — Buchanan Ingersoll & Rooney PC

(57) ABSTRACT

A physiological signal monitoring method includes steps that involve: acquiring samples of at least one digitized physiological signal through the use of a device carried by a user; detecting events within the digitized physiological signal by means of the device and extracting characteristics of the detected events by means of the device; searching for an anomaly in the events and characteristics of the extracted events by means of the device; and, via an encrypted wireless link, transmitting the digitized physiological signal by means of the device to a server via a mobile terminal when an anomaly is detected. If an anomaly is not detected, the digitized physiological signal is deleted by the device.

15 Claims, 7 Drawing Sheets

Figure 1:
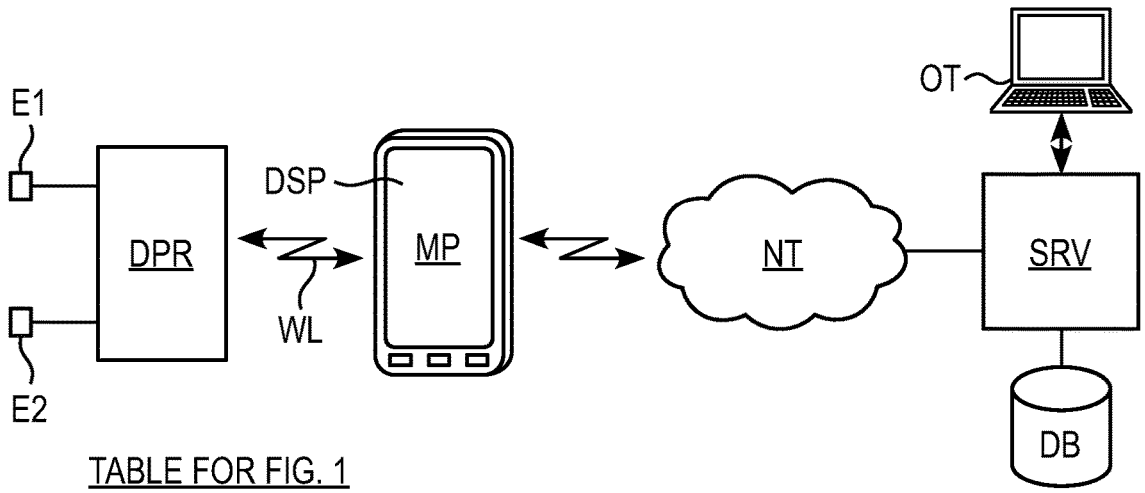

TABLE FOR FIG. 1
DPR  Processing Circuit
SRV  Server

(51) Int. Cl.
*A61B 5/053* (2021.01)
*G16H 40/67* (2018.01)
*A61B 5/08* (2006.01)
*A61B 5/085* (2006.01)
*A61B 5/318* (2021.01)
*A61B 5/339* (2021.01)
*A61B 5/364* (2021.01)
*A61B 5/366* (2021.01)
*A61B 5/0245* (2006.01)

(52) U.S. Cl.
CPC ............... *A61B 5/053* (2013.01); *A61B 5/08* (2013.01); *A61B 5/085* (2013.01); *A61B 5/318* (2021.01); *A61B 5/339* (2021.01); *A61B 5/364* (2021.01); *A61B 5/366* (2021.01); *A61B 5/486* (2013.01); *A61B 5/6805* (2013.01); *A61B 5/6843* (2013.01); *A61B 5/746* (2013.01); *A61B 5/747* (2013.01); *G16H 40/67* (2018.01); *A61B 5/02455* (2013.01); *A61B 5/0809* (2013.01); *A61B 5/0816* (2013.01); *A61B 5/6898* (2013.01)

(58) Field of Classification Search
CPC ..... A61B 5/6843; A61B 5/486; A61B 5/0472; A61B 5/0468; A61B 5/044; A61B 5/0006; A61B 5/6805; A61B 5/053; A61B 5/746; A61B 5/6898; A61B 5/0816; A61B 5/0809; A61B 5/02455; G16H 40/67
See application file for complete search history.

(56) References Cited

U.S. PATENT DOCUMENTS

| | | | | |
|---|---|---|---|---|
| 2007/0273504 | A1* | 11/2007 | Tran | A61B 5/0022 340/539.12 |
| 2013/0116514 | A1* | 5/2013 | Kroner | A61B 5/01 600/301 |
| 2014/0318699 | A1* | 10/2014 | Longinotti-Buitoni | A61B 5/0002 156/247 |
| 2016/0235344 | A1* | 8/2016 | Auerbach | A61B 5/087 |
| 2016/0287140 | A1* | 10/2016 | Beyar | A61B 5/091 |
| 2019/0022400 | A1* | 1/2019 | Kumar | A61B 5/0205 |

\* cited by examiner

TABLE FOR FIG. 1
DPR    Processing Circuit
SRV    Server

Figure 2:
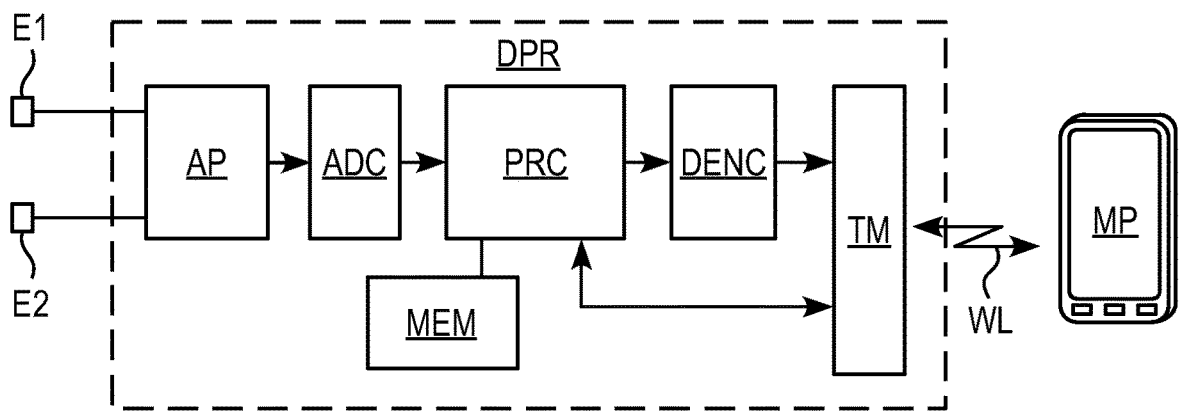

TABLE FOR FIG. 2
DPR    Processing Circuit
AP     Analog Circuit
PRC    Processor
DENC   Encryption Circuit
TM     Transmission Interface Circuit

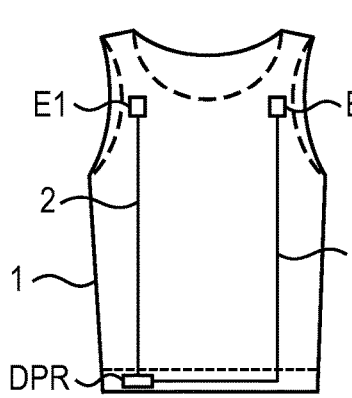

FIG. 3A

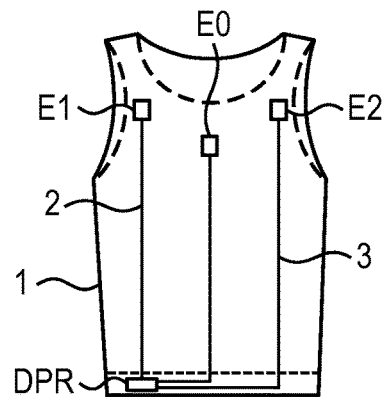

FIG. 3B

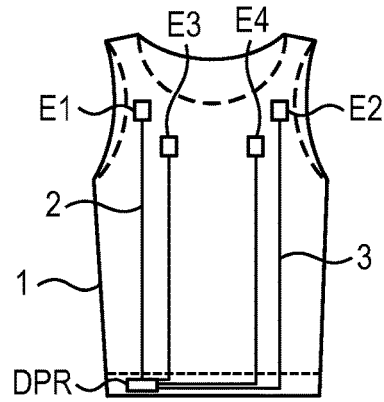

FIG. 3C

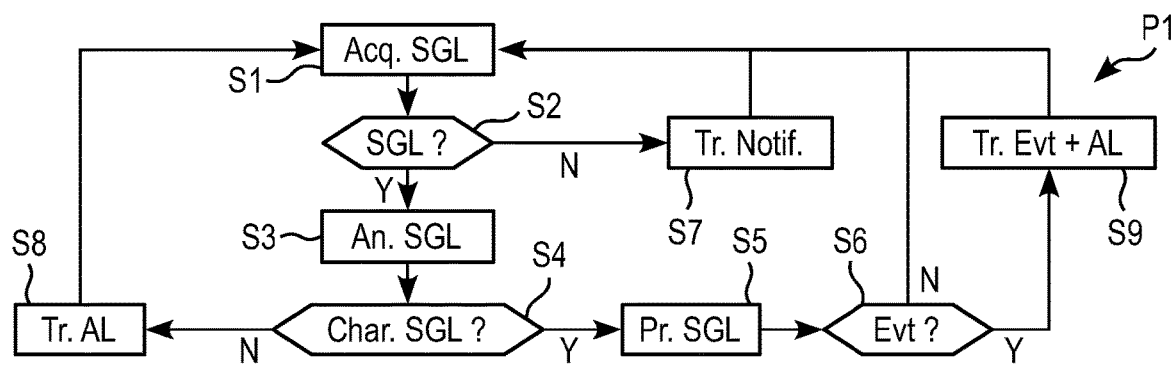

TABLE FOR FIG. 4
S1 - processor PRC receives samples of digitized signal SGL
S2 - processor PRC determines whether the signal SGL represents physiological signals of a human
S3 - processor analyzes the digitized signal SGL
S4 - are characteristic elements detected in the received signal SGL?
S5 - the processor PRC processes the signal SGL
S6 - the temporal section of the digitized signal is erased

FIG. 4

FIG. 6

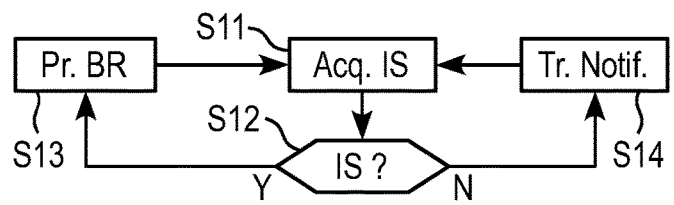

TABLE FOR FIG. 6
S11 - another signal IS is processed
S12 - the signal IS is analyzed to determine whether electrodes are in contact with the skin
S13 - Processor detects respiratory rate BR
S14 - Processor transmits notification

FIG. 7

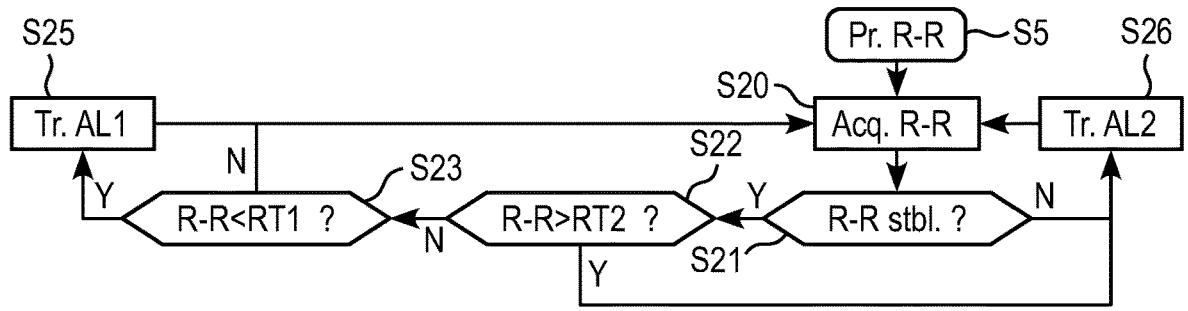

TABLE FOR FIG. 7
S5   the processor processes signal
S20  processor detects when R waves of ECG signal occur
S21  processor evaluates stability of R-R heart rate (is R-R stable?)
S22  processor compares the R-R heart rate with an upper threshold value RT2
S23  processor compares the R-R heart rate with a lower threshold value RT1
S25  processor sends the alarm signal AL1
S26  processor transmits the alarm signal AL2

FIG. 8

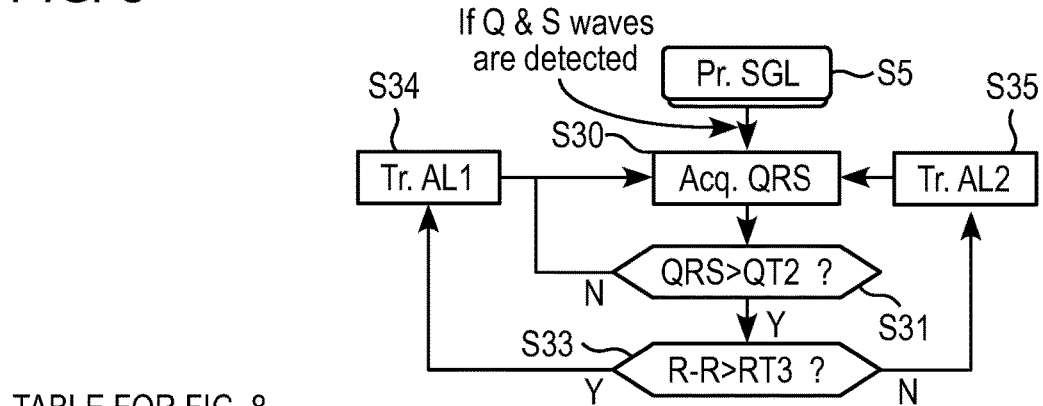

TABLE FOR FIG. 8

S5  processor processes signal SGL
S30 processor analyzes QRS complex
S31 processor compares QRS with an upper threshold value QT2
S33 processor compares the R-R heart rate with a threshold value RT3
S34 Processor transmits alarm signals AL1
S35 Processor transmits alarm signals AL2

FIG. 9

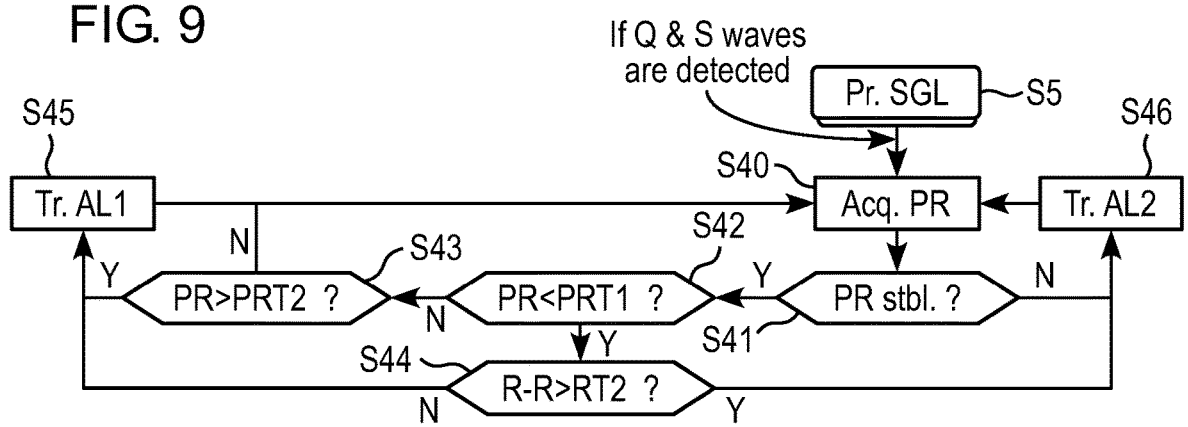

TABLE FOR FIG. 9

S5  processor processes signal SGL
S40 processor analyzes PR segment
S41 stability of duration of PR segment is analyzed for a certain time
S42 processor compares duration of PR segment with lower threshold value PRT1
S43 Is duration of PR segment greater than upper threshold value PRT2
S44 processor PRC compares R-R heart rate with threshold value RT2
S45 Processor transmits signal AL1
S46 Process transmits signal AL2

Figure 10:
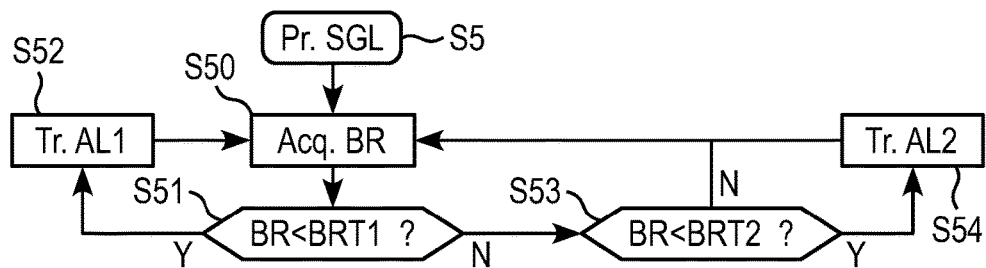

TABLE FOR FIG. 10
S5   processor processes signal SGL
S50  the respiratory rate is extracted from the impedance signal
S51  processor PRC compares the respiratory rate BR with a lower threshold value BRT1
S52  Processor transmits signal AL1
S53  processor PRC compares respiratory rate BR with upper threshold value BRT2
S54  Processor transmits signal AL2

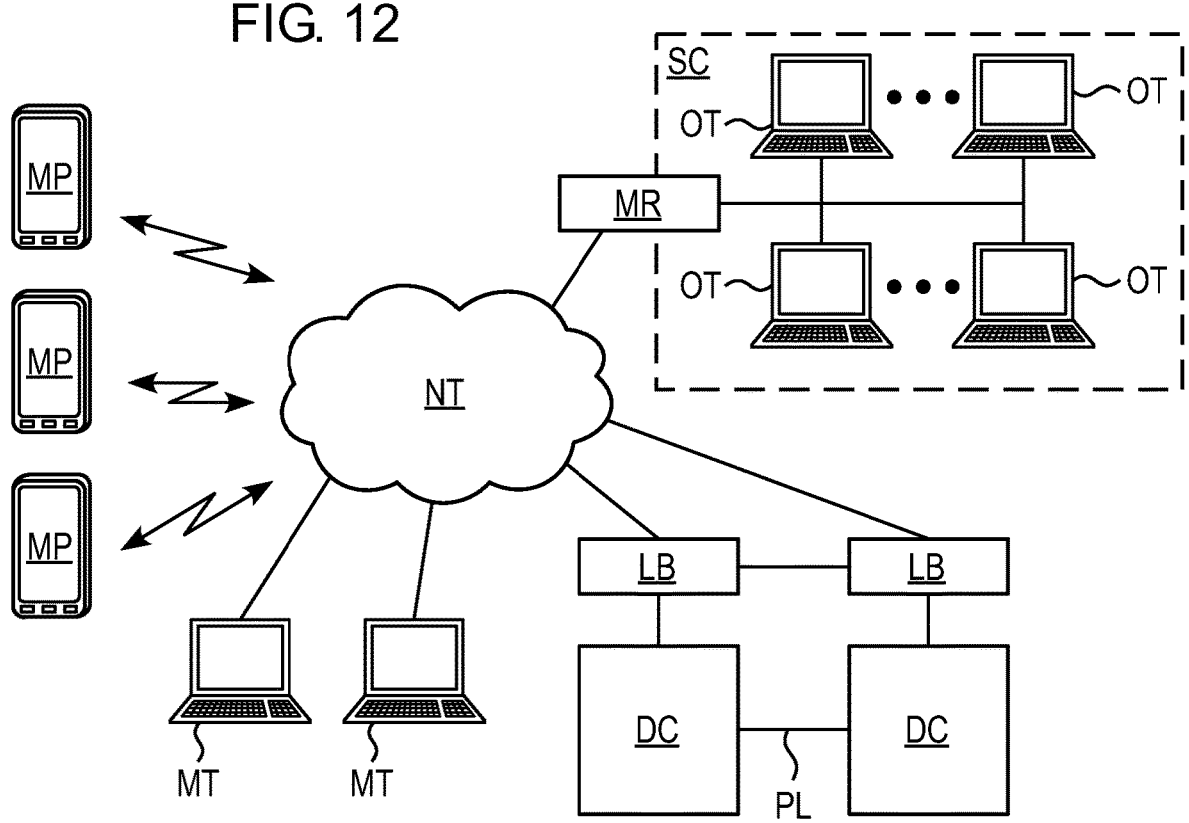

METHOD AND SYSTEM FOR ACQUIRING AND ANALYZING PHYSIOLOGICAL DATA

The present invention relates to systems for acquiring and monitoring physiological signals, such as signals relating to cardiac and pulmonary activity, and body temperature.

Generally, cardiac activity is monitored by placing electrodes on the patient's skin, by amplifying and by recording the electrical signals supplied by the electrodes, Recording these electrical signals makes it possible to create an electrocardiogram (ECG) representative of the electrical activity of the patient's heart. Nowadays, ECGs are commonly used to detect a certain number of pathologies that may affect the heart.

Portable devices for monitoring and recording chronologies of ECG data exist. Some of these devices are arranged in a Holter monitor, designed to be carried by the patient, for example attached to his belt, this monitor being connected, by wires, to electrodes positioned on the patient's skin. These devices thus make it possible to record cardiac activity throughout the day without disturbing the patient's everyday activities. The data that are recorded may then be post-analyzed in order to establish a medical diagnosis for the patient. These devices therefore exhibit the major drawback of not allowing real-time monitoring of the state of the patient. Specifically, many pathologies linked to a cardiac disorder could be prevented if the cardiac anomaly were to be detected and treated in time. These devices are also relatively heavy and bulky, and the electrodes are easily inadvertently detached, such that they are not able to be worn in particular during periods when the patient is sleeping.

Devices in the form of a wristwatch also exist, which devices are designed to be worn permanently, in particular during a sporting activity. However, these devices are generally limited to acquiring and displaying heart rate, this information not being sufficient to detect certain heart pathologies.

It has already been proposed to transmit ECG data or data extracted from the ECG data, such as heart rate data, from a small acquisition module to a mobile terminal such as a smartphone using a wireless link, for example of Bluetooth type. The telecommunication functions of the mobile terminal may be utilized to transmit these data to a medical monitoring center. However, in order to avoid draining the battery of the acquisition device and of the mobile terminal in particular, it is desirable to limit the amount of data thus transmitted. This constraint also aims to allow several patients to transmit ECG data to one and the same monitoring center, without requiring excessive data storage and transmission means in the monitoring center. Thus, when ECG data do not make it possible to detect any pathology, either because they correspond to a normal ECG signal or because they are disrupted to too great an extent, it is not necessary to transmit them to the monitoring center. However, it is necessary to avoid what are termed 'false-negative' cases in which ECG data may be erroneously discarded and therefore not transmitted to the monitoring center, or not recorded locally by the device carried by the patient, if it is temporarily not possible to transmit the ECG data to the monitoring center. It is also desirable to limit the amount of ECG data transmitted to the monitoring center for analysis by a human operator, this in order to limit the amount of ECG data to be analyzed and thus limit the required number of human operators responsible for manually analyzing ECG data.

It is therefore desirable to make it possible to acquire physiological signals of sufficiently good quality to allow the establishment of a reliable diagnosis regarding a patient's state of health. It is also desirable for this acquisition of physiological signals to be able to be carried out over long periods of longer than one day, and preferably over several days, so as to be able to permanently monitor a patient's state of health. It is also desirable for the device responsible for acquiring the physiological signals to be able to be installed easily on a patient for several days, without disturbing his well-being in particular during periods of sleep, and to be compatible with all common activities, and in particular taking part in sporting activities.

It may also be desirable to process physiological signals in real time so as to detect anomalies therein that are liable to indicate a pathology, and to transmit them to a monitoring center only when such an anomaly is liable to be detected. It may also be desirable for this anomaly detection to be carried out while avoiding cases of false negatives and while limiting cases of false positives.

Embodiments relate to a method for monitoring physiological signals, comprising steps consisting in: acquisition of samples of at least one digitized physiological signal, using a device carried by a user, detection, by the device, of events in the digitized physiological signal and extraction, by the device, of characteristics of the detected events, searching, by the device, for an anomaly in the events and the extracted event characteristics, and transmission, via a wireless link in encrypted form, of the digitized physiological signal, by the device, to a server via a mobile terminal when an anomaly is detected or when an enhanced monitoring mode is activated, and otherwise the digitized physiological signal is erased by the device.

According to one embodiment, the method comprises steps of: acquiring a signal of impedance variation between electrodes in contact with the user's skin, comparing the impedance variation signal with a threshold value, transmitting a notification to the user by way of the mobile terminal so as to inform said user that the electrodes are not in contact with his skin, when the impedance variation signal does not exceed the threshold value, and extracting a respiratory rate of the user from the impedance variation signal when the impedance variation signal exceeds the threshold value.

According to one embodiment, the method comprises steps of comparing the respiratory rate with lower and upper threshold values, and of detecting an anomaly if the respiratory rate is not between the lower and upper threshold values.

According to one embodiment, the characteristics of events detected in the digitized physiological signal comprise parameters extracted from the digitized physiological signal, an anomaly being detected if one of the extracted parameters does not belong to a window centered on a mean value of a corresponding parameter extracted from a reference digitized signal.

According to one embodiment, the method comprises a step of determining a treatment priority level for a detected anomaly, from among two priority levels, the anomalies of the higher priority level being shown on an operator terminal before the anomalies of the lower priority level.

According to one embodiment, the digitized physiological signal comprises an electrocardiogram signal, the detected events are R, P, Q, S and T waves, and the characteristics extracted from the events relate to the respective amplitudes of these waves and/or to the duration of the time intervals between these waves.

According to one embodiment, the R waves are detected in the digitized physiological signal by comparing the electrocardiogram signal with a threshold value, and the P, Q, S and T waves are sought in windows determined on the basis of an instant of detection of an R wave.

According to one embodiment, the method comprises steps of: determining a heart rate by counting the number of R waves per unit of time, an anomaly being detected if the measured heart rate has an instability greater than a first instability threshold value, or if the measured heart rate is not between first and second heart rate threshold values, and/or steps of: determining a duration between the Q and S waves, and comparing the duration between the Q and S waves with a threshold value for the duration between the Q and S waves, an anomaly being detected if the duration between the Q and S waves is greater than the threshold value for the duration between the Q and S waves, and/or steps of: determining a duration between the P and R waves, comparing an instability of the duration between the P and R waves with a second instability threshold value, comparing the duration between the P and R waves with two threshold values for the duration between the P and R waves, and detecting an anomaly if the instability of the duration between the P and R waves is greater than the second instability threshold value or if the duration between the P and lit waves is not between the two threshold values for the duration between the P and R waves.

According to one embodiment, the method comprises steps of: detection, by the server, of events in the received digitized physiological signal, and extraction, by the server, of detected event characteristics, searching, by the server, for an anomaly in the events and the extracted event characteristics, and transmission, by the server, of the received digitized physiological signal to an operator terminal when an anomaly is detected by the server.

According to one embodiment, the method comprises steps of: rendering and displaying of the physiological signal by an operator terminal on the basis of the digitized physiological signal received by the server, and transmission, to the mobile terminal, of a notification sent by the operator terminal and relating to the physiological signal shown on the display screen, and transmission of the notification to the user by way of the mobile terminal.

According to one embodiment, the notifications sent by the operator terminal to the mobile terminal comprise at least one of the following elements: an order to activate the enhanced monitoring mode that is transmitted from the mobile terminal to the device, the device transmitting the digitized physiological signal upon receipt of the activation order and for as long as the enhanced monitoring mode is activated, a notification to be transmitted from the mobile terminal to the user so as to inform the user that he should consult his doctor, a notification to be transmitted from the mobile terminal to the user so as to inform the user that he should await the emergency services or visit a hospital immediately, and a notification containing parameters for detecting anomalies in the events and the extracted event characteristics, which notification is transmitted from the mobile terminal to the device, the device using the received anomaly detection parameters to detect anomalies.

Embodiments may also relate to a device for monitoring physiological signals, configured to be carried by the user and to acquire, in real time, a digitized physiological signal, and transmit the digitized physiological signal to a server via a mobile terminal, this device being configured to implement the method such as defined above.

According to one embodiment, the device comprises electrodes and/or a sensor integrated into a garment, an analog processing circuit connected to the electrodes and/or to the sensor by way of conductive links integrated into the garment, a digital processing circuit connected to the analog processing circuit, and a transceiver circuit connected to the digital processing circuit, the transceiver circuit being configured to communicate with the mobile terminal.

According to one embodiment, the electrodes are placed in the garment so as to come into contact with the user's skin in the region of the shoulder blades or of the sides level with the sternum, the electrodes being formed by printing on the garment, and the conductive links being formed by a conductive wire coated with an insulating layer and inserted into the fabric forming the garment.

Embodiments may also relate to a system for monitoring physiological signals, comprising: a server, a mobile terminal of a user, comprising a communication circuit for establishing communication with the server, a device carried by the user and configured to acquire, in real time, a digitized physiological signal, and transmit the digitized physiological signal to the server via the mobile terminal, the system being configured to implement the method defined above.

Figure 5A:
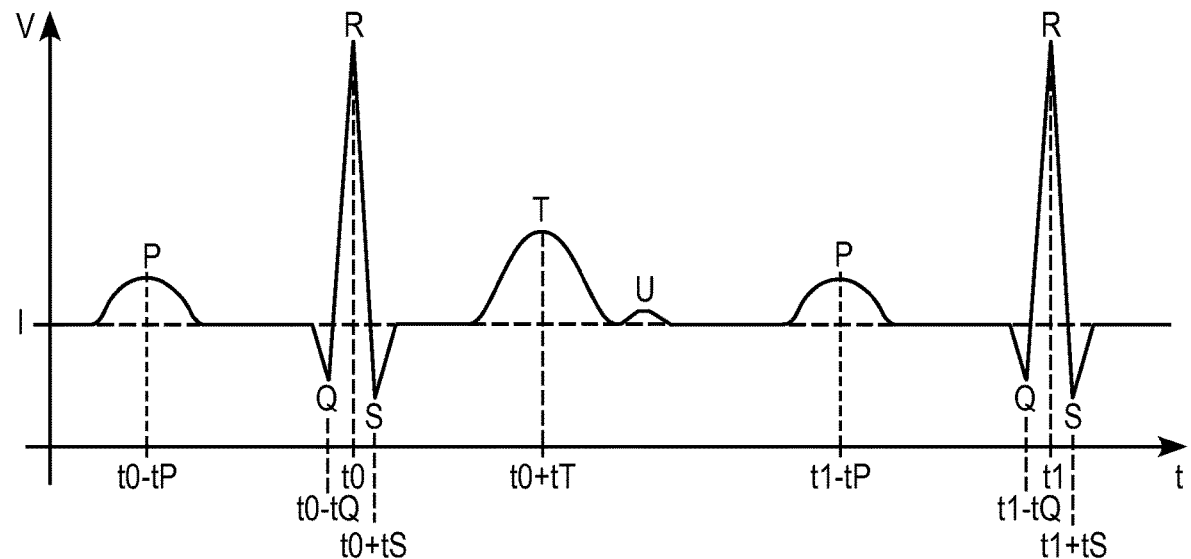
Figure 5B:
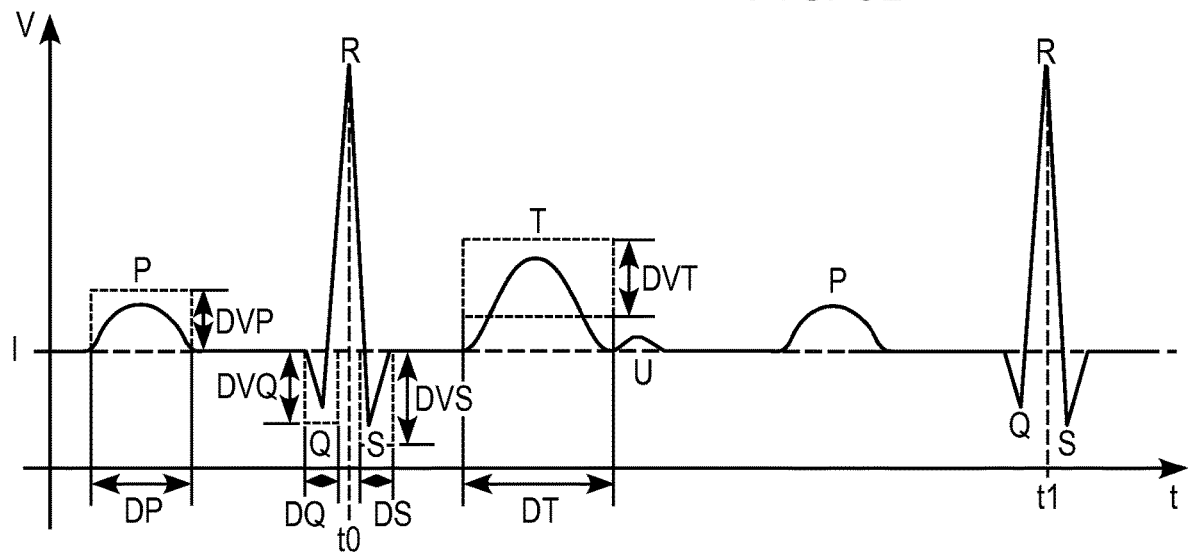
Figure 11:
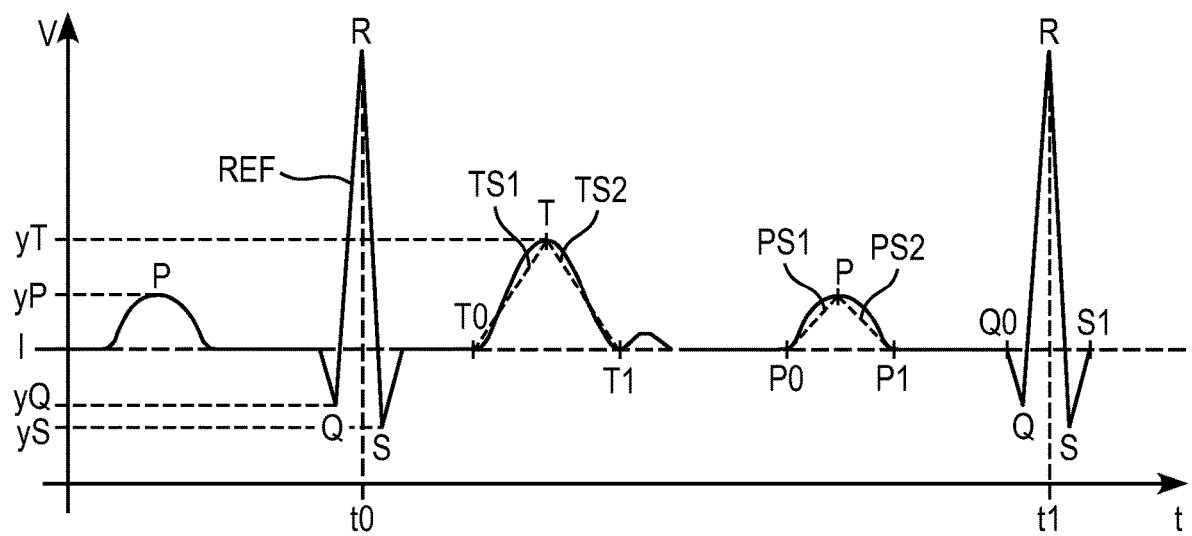

Exemplary embodiments of the invention will be described below, without limitation and with reference to the appended figures, in which:

FIG. 1 schematically shows a system for acquiring and for monitoring physiological signals obtained from a patient, according to one embodiment, FIG. 2 schematically shows a device for acquiring and for processing physiological signals and intended to be carried by a patient, according to one embodiment, FIGS. 3A, 3B and 3C schematically show a garment into which elements of the acquisition and processing device are integrated, according to various embodiments, FIG. 4 shows steps of procedures implemented in the acquisition and processing device, according to one embodiment, FIGS. 5A and 5B show a schematic waveform of an ECG signal, illustrating a method for analyzing such a signal, according to one embodiment, FIGS. 6 to 10 show steps of procedures implemented in the acquisition and processing device, according to various embodiments, FIG. 11 shows a schematic waveform of an ECG signal, illustrating a method for analyzing such a signal, according to another embodiment, FIG. 12 shows an exemplary embodiment of the hardware architecture of the acquisition system.

FIG. 1 shows a system for acquiring and for monitoring physiological signals obtained from a patient, according to one embodiment, for implementing a medical monitoring service. The acquisition and monitoring system comprises a device for acquiring physiological signals, carried by a patient and comprising sensors and/or electrodes E1, E2, a circuit DPR for processing signals supplied by the sensors and/or the electrodes E1, E2, a mobile terminal MP such as a smartphone, and a server SRV. The terminal MP and the circuit DPR communicate with one another by way of a wireless link WL, for example of BLE (Bluetooth Low Energy) type. The terminal MP and the server SRV communicate with one another by way of networks NT, such as the Internet and one or more mobile telephony networks. The sensors and the electrodes E1, E2 may comprise in particular one or more of the following elements: electrodes for capturing a heart rate and/or an electrocardiogram, and/or a galvanic skin response and/or a respiratory rate, a sensor for measuring the pH of the body, a sensor for measuring the temperature of the body, a blood pressure sensor, one or more sensors for detecting and/or measuring the concentration of chemical elements, such as glucose, tumor markers, pregnancy markers, etc.

The terminal MP may execute a dedicated application configured to send, to the processing circuit DPR, a waking signal via the link WL, detect the presence of the processing circuit DPR connected via the link WL, and display, on its screen, information relating to the presence of the processing circuit DPR connected via the link WL. This dedicated application is also configured to receive the data relating to the signals acquired by the processing circuit DPR and relay these data to the server SRV. This dedicated application is also configured to receive commands, for example from the server SRV, and relay them to the processing circuit DPR. The commands intended for the circuit DPR may comprise a command to update the software installed in the circuit DPR, commands to update operating parameters of the circuit DPR, or else commands that trigger for example the storage and the packet-switched transmission, for example every 12 or 24 hours, of acquired signals or of characteristics of these signals. This dedicated application is also configured to receive, from the server SRV, notifications to be presented to the patient on the display screen of the terminal MP. There may thus be provision for several notifications. These notifications may make it possible to trigger, from the server SRV, the displaying of messages on the screen of the terminal MP that inform the patient that he should consult his doctor urgently or non-urgently, or that he should visit a hospital immediately or await the arrival of emergency services. To this end, the terminal MP may comprise a geographical location circuit, such as GPS (Global Positioning System), the dedicated application being configured to transmit, upon request from the server SRV, the geographical position supplied by the location circuit of the terminal.

The server SRV is connected to a database DB in which are stored data relating to patients carrying devices for acquiring physiological signals, and data relating to the physiological signals transmitted by these devices.

FIG. 2 shows the processing circuit DPR, according to one embodiment. The circuit DPR comprising an analog processing circuit AP connected to the sensors and/or to the electrodes E1, E2, an analog-to-digital conversion circuit ADC, a processor PRC, and a transmission interface circuit TM. The analog circuit AP comprises one analog signal processing channel per signal to be processed. Each signal processing channel comprises in particular one or more filters and a signal amplifier. The circuit ADC receives the signals processed by the circuit AP, digitizes them and supplies the digitized signals to the processor PRC. The signals may be digitized on 12 or 16 bits with a sampling frequency set between 25 and 800 Hz, depending on the type of signal to be processed. For an ECG signal, the sampling frequency may be set for example at 500 Hz. The processor PRC processes the digitized signals supplied by the conversion circuit ADC so as to develop physiological data to be transmitted by the interface circuit TM. The processor PRC may comprise a microprocessor or a microcontroller, and may be connected to one or more memories MEM of volatile and/or non-volatile type, in particular in order to store the physiological data that it has developed on the basis of the signals received from the circuit ADC.

The circuit DPR may also comprise an encryption circuit DENC for encrypting the physiological data developed by the processor PRC, before transmitting said data using the transmission interface circuit TM. To this end, the encryption circuit DENC may use a symmetric encryption key known only to itself and the server SRV, or an asymmetric public encryption key corresponding to a private key known only to the server SRV. According to one embodiment, the circuit DENC implements the AES (Advanced Encryption Standard) algorithm using a 256 or 512 bit encryption key.

The processor PRC may be configured by a program stored in memory to process the digitized signals supplied by the circuit ADC, to detect events therein, command encryption thereof by the circuit DENC, transmit them to the terminal MP, and record them upon a command received from the terminal MP.

Of course, the system may comprise further acquisition channels connected to electrodes or sensors, each acquisition channel comprising an analog circuit comprising one or more filters, one or more signal amplifiers, and possibly an analog-to-digital converter.

FIGS. 3A, 3B and 3C show a garment 1, such as an undergarment (T-shirt), into which the processing circuit DPR, the electrodes E1, E2, and electrical connection links 2, 3 between the electrodes E1, E2 and the circuit DPR are integrated. The electrodes E1, E2 are positioned on the garment 1 at a location where they are guaranteed to remain in contact with the patient's skin, for example in the region of the shoulder blades as shown in FIGS. 3A, 3B and 3C, or in the anterior region of the sides level with the sternum (D1 derivation in medical ECG). The circuit DPR may for example be housed with a rechargeable battery for example in a lining or a hem of the garment 1, or else in a pocket formed in the garment. The connection between the battery and an external circuit for charging the battery may be made through inductive coupling. The garment 1 may also be a jersey, a life jacket, a bra or a chest band.

According to one embodiment, the electrodes E1, E2 are dry electrodes. They may be produced using a technique of printing or applying paint onto the fabric of the garment 1 (or onto a coating made of PDMS—polydimethylsiloxane—deposited on the fabric), using an electrically conductive ink, for example based on PEDOT:PSS (poly(3,4-ethylenedioxythiophene) polystyrene sulfonate). To ensure good electrical contact with the skin, the electrodes may be coated with an ionic gel (ionic conductive liquid trapped in a polymer matrix) that may also be deposited using a printing or paint application technique. The electrodes E1, E2 may also be made from a metal material, such as stainless steel or gold, and fastened by any means on the garment, their contact with the skin being promoted through the positioning thereof (shoulder blades, sides).

The electrical links 2, 3 may be produced using a conductive wire (Al, Au, Ag, Cu) coated with an electrically insulating layer, and knitted or woven with the threads forming the fabric of the garment 1, or laminated on the garment, or else housed in textile pockets formed on the garment. Thus, the wire forming the electrical links 2, 3 may be insulated by being soaked in a resin such as PET (polyethylene terephthalate).

The circuit DPR may be formed on a flexible carrier and be embedded in a sealtight and flexible material. Thus, the circuit DPR may be formed on a substrate for example made of PDMS, PET or polyimide, and encapsulated in one of these materials or in alumina. The components forming the circuit DPR may be thinned and deposited, without being encapsulated, on the substrate using the pick and place method. The various components forming the circuit DPR may comprise the analog circuit AP and the converter ADC, the microcontroller PRC including the encryption function ENC, the (Bluetooth or BLE) communication module IM, a battery or a rigid, deformable or flexible high-capacity capacitor, Bluetooth/BLE antennae and an antenna coil for inductively recharging the battery. The circuit DPR may be encapsulated using an atomic layer deposition (ALD) method. The connections between the electrodes E1, E2, the wires 2, 3 and the circuit DPR may be produced by reflow soldering, or more generally using a wire-bonding and/or flip-chip technique.

According to one embodiment, the analog processing circuit AP may be produced not in the circuit DPR, but in association with one and/or the other of the electrodes E1, E2. The circuit AP may thus be configured to generate an analog signal capable of being transmitted without excessive degradation by the wires 2, 3 to the circuit DPR.

FIG. 4 shows steps S1 to S9 of a procedure P1 for the analysis of signals by the processor PRC, according to one embodiment. The analyzed signals are supplied by the conversion circuit ADC. Steps S1 and S2 are executed first. In step S1, the processor PRC receives samples of a temporal section of a digitized signal SGL, for example with a duration between around ten seconds and one minute. In step S2, the processor PRC determines whether the acquired signal SGL is representative of physiological signals of a human, or in other words whether the electrodes E1, E2 are indeed in contact with the patient's skin, or whether the sensors are indeed receiving physiological signals. If the acquired signal is not representative of physiological signals of a human, the processor PRC executes step S7, and otherwise it executes steps S3 and S4. In step S3, the processor analyzes the received digitized signal SGL so as to search therein for characteristic elements to be measured. In step S4, if sought characteristic elements are detected in the received signal SGL, the processor PRC executes steps S5 and S6, and otherwise it executes step S8. In step S5, the processor PRC processes the signal SGL and the detected characteristic elements of the signal in order to detect anomalies therein. In step S6, if no anomaly is detected, the temporal section of the digitized signal SGL thus analyzed is erased, and the procedure P1 is executed again starting from step S1 in order to acquire and analyze a new temporal section of the digitized signal SGL. By contrast, if an anomaly is detected in step S6, the processor PRC executes step S9, in which it triggers or continues monitoring operations depending on the severity of the anomaly, such as the transmission and/or the storage of the received signal SGL for a certain time, and/or the transmission of an alarm signal AL to the server SRV. In step S7, an alarm message is transmitted to the terminal MP in order to trigger the displaying, on the screen of the terminal, of a notification alerting the patient that the electrodes and/or the sensors are not positioned properly. The terminal MP may also relay the alarm message to the server SRV.

In step S8, the signal SGL received by the processor PRC has a form that is excessively far from an expected form, and an alarm signal AL may then be transmitted to the mobile terminal MIP and/or to the server SRV. Depending on the nature of the signal, it may also be decided to store or to transmit the signal SGL to the server SRV via the mobile terminal MP. Following the execution of one of steps S6, S7, S8 and S9, the procedure P1 is executed again starting from step S1 in order to acquire and analyze a new temporal section of the digitized signal SGL.

If the link with the terminal MP is absent, the processor PRC may store the data to be transmitted, that is to say the received signal SGL and/or characteristic elements extracted from the received signal, and also the alarm messages, while waiting for the link to be re-established.

The detection of anomalies may consist in comparing the digitized signal SGL with a reference digitized signal, or in comparing characteristics extracted from the signal SGL with the corresponding ones extracted from the reference signal. The reference signal may have been determined on the basis of one or more signals acquired from the patient himself, for example in various situations, at a time when said patient is healthy.

FIGS. 5A and 5B show a characteristic waveform of a normal ECG signal, comprising two heartbeats, such as is able to be supplied by the analog processing circuit AP. This waveform comprises P, Q, R, S, T and U waves extending from a baseline voltage I, called 'isopotential line', generally detected between the T or U wave and the P wave of the following heartbeat. The R waves occur at instants t0, t1, etc. (FIG. 5A), and take the form of a peak in the direction of the positive voltages. As the R waves have a higher amplitude than all of the other P, Q, S, T and U waves, and a relatively short duration, they are generally used to determine heartbeat. The P waves occur at instants tj-tP (j=0, 1, etc.), that is to say a certain time tP before the R waves. The P waves have a rounded form of relatively long duration DP (FIG. 5B), greater than the duration of the R waves, and of relatively low amplitude in the direction of the positive voltages. The Q waves occur at instants tj-tQ (j=0, 1, etc.), that is to say a certain time tQ before the waves. The Q waves have the form of a peak in the direction of the negative voltages, of relatively short duration and of low amplitude. The S wave follows the R wave at instants tj+tS (j=0, 1, etc.), a certain time tS after the R wave, and has the form of a peak in the direction of the negative voltages. The Q and S waves have substantially one and the same duration and one and the same amplitude. The T wave occurs at instants tj+tT (j=0, 1, etc.), a certain time tT after the R wave. The T wave has a rounded form in the direction of the positive voltages, a relatively high amplitude situated between those of the P and R waves, and a duration DT greater than that of the P wave. The U wave is a small wave of rounded form in the direction of the positive voltages immediately following the T wave. The U wave is absent from ECG signals in 25% to 50% of cases.

Certain characteristics of an ECG signal may be analyzed in order to detect pathologies. It is thus known to analyze the amplitude and the duration of the P wave, the duration of the PR segment between the end of the P wave and the start of the Q wave, the duration of the PR interval between the start of the P wave and the start of the Q wave, the duration of the QRS complex between the start of the Q wave and the end of the S wave, the form and the duration of the ST segment between the end of the S wave and the start of the T wave, the form of the T wave, the duration of the QT segment between the start of the Q wave and the end of the T wave, and also the form of the U wave, where applicable.

If the signal is an ECG signal, step S2 in FIG. 4 may comprise searching for the presence of the R waves in the signal SGL. Step S3 may comprise searching for the presence of the P, Q, S and T waves in the signal SGL. Step S5 may be executed if at least one of these waves is detected in the signal SGL. Step S8 is executed if none of the P, Q, S and T waves are able to be detected in the signal SGL. In step S7, executed when the R waves are not detected, another signal may be analyzed in order to determine whether the electrodes E1, E2 are in contact with the patient's skin. The processing operation performed in step S7 depends on this detection. Thus, if the electrodes E1, E2 are not detected in contact with the skin, the processor PRC sends, to the terminal MP, a notification to be displayed on the screen of the terminal so as to inform the patient that he should put on the garment 1. If the electrodes are detected in contact with the patient's skin, the processor PRC sends an alarm signal AL, to the server SRV via the terminal MP.

In the case of an ECG signal, step S2 may consist in comparing the samples of the digitized signal with an RT threshold voltage value (FIG. 5A), for example set at I+0.3 mV, the R waves being considered to be detected when the voltage of the ECG signal exceeds the RT threshold value. If the comparison of the ECG signal allows a heart rate to be extracted, the processor PRC looks to detect the other P, Q, S and T waves in step S3. These waves may be detected on the basis of each R wave detected at the instants tj (j=0, 1, etc.). Thus, the peak of the P wave may be detected by looking for a maximum value within the temporal interval [tj−tP−DP/2, tj−P+DP/2] (j=0, 1, etc.). The peak of the Q wave may be detected by looking for a minimum value within the temporal interval [tj−tQ−DQ/2, tj+tQ+DQ/2]=0, 1, etc.). The peak of the S wave may be detected by looking for a minimum value within the temporal interval [tj+ts−DS/2, tj+tS+DS/2]=0, 1, etc.). The peak of the T wave may be detected by looking for a maximum value within the temporal interval [tj+tT−DT/2, tj+tT+DT/2] (j=0, 1, etc.). For a healthy human, the values tP and DP may be for example set respectively at 145 ms and 130 ms, the values tQ and DQ may be for example set respectively at 60 ms and 20 ms, the values tT and DS may be for example set respectively at 60 ms and 20 ms, and the values tT and DT may be for example set respectively at 300 ms and 200 ms.

According to one embodiment, the processor PRC verifies in step S5 that the respective amplitudes of the P, Q, S and T waves are situated within particular ranges. If this is not the case (step S6), an anomaly is considered to be detected and step S9 is executed. Thus, the processor PRC verifies that the maximum value of the P wave is situated within the interval [0, DVP], that the minimum value of the Q wave is situated within the interval [−DVP, 0], that the minimum value of the S wave is situated within the interval [−DVS, 0], and that the maximum value of the T wave is situated within the interval [mT, mT+DVT]. For a healthy human, the values DVP and DVQ, DVS, DVT and mT are for example set respectively at 1+0.25 mV, 1+0.3 mV, 1+0.5 mV, 1+0.25 mV and 1+0.05 mV.

If in steps S5 and S6 the peaks of the P, Q and T waves are not located within the windows defined above, the processor PRC sends, via the interface TM to the server SRV, the signal SGL and an alarm signal AL1 that makes it possible to bigger monitoring of the ECG signals (step E9). If the R waves are not detected (crossing of the RT threshold) and if the peaks of the S waves are not located within the windows defined above, the processor PRC sends, via the interface TM to the server SRV, the signal SGL and an alarm signal AL2 with a severity level higher than the alarm signal AL1 (step S9). The alarm signals AL1 and AL2 are transmitted to the terminal OT of an operator connected to the server SRV. The alarm signals AL1, AL2 make it possible to define different priority levels for the processing of the associated signals SGL, the signals SGL associated with the alarm signal AL2 being processed with priority by an operator connected to the server SRV.

In step S5, the processor PRC may also verify the form and the duration of the ST segment between the end of the S wave and the start of the T wave. If these elements of the signal SGL are not as expected, the processor PRC sends, via the interface TM to the server SRV, the signal SGL and an alarm signal. For example, the conformity of the ST segment may consist in verifying that, at the instants tj+100 ms (j=0, 1, etc.), the voltage of the signal SGL is greater than 1−0.02 or is between this value and I+0.02 mV (ST segment present at the voltage I) and that, between the instants tj+200 ms and tj+400 ms, the signal SGL has one or more values greater than the voltage I (for example 0 mV) indicative of the presence of the T wave. If the ST segment at the voltage I is absent, the processor PRC may send, via the interface TM to the server SRV, the signal SGL and the alarm signal AL2. If the T wave is absent, the processor PRC may send, via the interface TM to the server SRV, the signal SGL and the alarm signal AL1.

If the R waves are detected, the processor PRC may also calculate and store, in step S3, the mean and the standard deviation of the heart rate during each period of around ten seconds to one minute, and send these data in packet-switched form to the server SRV for example every 12 or 24 hours.

FIGS. 6 to 9 show further steps of procedures for analyzing characteristic elements of an ECG signal and for processing anomalies, which steps may also be executed during step S2 or S5 of the procedure P1.

FIG. 6 shows steps S11 to S14 that may be executed during steps S1, S2, S3 and S7, respectively, of the procedure P1. In step S11, another signal IS, acquired by the circuits AP, ADC, is processed by the processing circuit DPR. The period of acquisition of the signal IS may be identical to that of the signal SGL, such that the signals IS and SGL are acquired alternately. The signal IS may be representative of the patient's respiratory activity. This signal may be acquired for example by continuously measuring the impedance between the electrodes E1 and E2 (FIG. 3A). To this end, a current with a magnitude of between 5 and 100 µA at a frequency of between 1 and 40 kHz may for example be sent between the electrodes E1, E2. The impedance measurement may then be obtained from a measurement of voltage between the electrodes. Typically, the impedance thus liable to be measured varies between −0.1 and +0.1 ohm around a central value situated between 0.1 and 1 kohm.

In step S12, the signal IS is analyzed in order to determine whether the electrodes E1, E2 are in contact with the skin and whether this signal is representative of a respiratory rate. It may be determined that the electrodes E1, E2 are in contact with the skin if the signal IS remains below a first impedance threshold value, for example 2 kohm. If the electrodes E1, E2 are not detected in contact with the patient's skin, the processor executes step S14 (or S7), in which it transmits, to the mobile terminal MP, a notification intended to alert the patient that the electrodes are not in contact with his skin. This notification may also be transmitted to the server SRV. If, in step S12, an impedance signal is indeed detected, this means that the electrodes E1, E2 are indeed in contact with the patient's skin and that the signal SGL is indeed being measured on the patient. The processor then executes step S13, in which it seeks to detect the respiratory rate BR. The respiratory rate BR may be obtained by comparing the signal IS with a second impedance threshold value, and by counting the number of times per unit of time that the signal IS exceeds the threshold value, which value is set for example at 500 ohm. At the end of steps S13 and S14, the processor PRC executes step S11 again.

As illustrated in FIG. 3B, a third electrode E0 serving as a reference electrode may be provided. Trans-thoracic impedance values are measured between each of the electrodes E1, E2 and the reference electrode E0 in order to determine trans-thoracic impedances between the electrode E1 and the reference electrode, on the one hand, and between the electrode E2 and the reference electrode, on the other hand (DII and DII derivations in medical ECG). The electrode E0 may also be used to measure the signal SGL corresponding to the variations in the voltage between the electrodes E1 and E0 and between the electrodes E2 and E0. Of course, each electrode E1, E2 may be associated with a separate reference electrode in order to perform these impedance and voltage measurements. Thus, as illustrated in FIG. 3C, the electrode E1 is associated with a first reference electrode E3, and the electrode E2 is associated with a second reference electrode E4. Trans-thoracic impedance values are measured between the electrode E1 and the reference electrode E3 and between the electrode E2 and the electrode E4 in order to determine trans-thoracic impedances between the electrodes E1 and E3 and between the electrodes E2 and E4.

FIG. 7 shows steps S20 to S26 of analyzing the heart rate, which steps are executed when said heart rate has been detected in the signal SGL. These steps may be executed in step S5 of the procedure P1. In step S20, the processor PRC detects the instants at which the R waves of the ECG signal occur. In step S21, the processor PRC evaluates the stability of the R-R heart rate for a certain time, for example between around ten seconds and one minute, while determining whether it remains within an interval of for example between −15% and +15% around a mean value. In step S21, if the heart rate is stable, the processor PRC executes step S22, and otherwise it executes step S26. In step S22, the processor PRC compares the mean R-R heart rate with an upper threshold value RT2. If the mean R-R heart rate derived from the detection of the R waves is greater than the threshold value RT2, the processor PRC executes step S26, and otherwise it executes step S23. In step S23, the processor PRC compares the mean R-R heart rate with a lower threshold value RTI. If the mean R-R heart rate is lower than the threshold value RT1, the processor PRC executes step S25, and otherwise (the R-R heart rate is between the threshold values RT1 and RT2) the heart rate continues to be monitored by executing steps S20 and S21 again. The threshold values RT1, RT2 depend on the patient's profile. For a healthy human, the threshold values RT1 and RT2 are for example set at 400 ms and 1600 ms, respectively, for the duration between two consecutive R waves, that is to say 50 and 150 beats per minute, respectively. In step S25, the processor PRC sends, via the interface TM to the server SRV, the signal SGL and the alarm signal AL1, making it possible to trigger monitoring of the ECG signals by a human operator having a terminal connected to the server SRV. In step S26, the processor PRC transmits, to the server SRV, the signal SGL and the alarm signal AL2.

Moreover, the reception of the alarm signals AL1, AL2 by the server SRV may trigger the transmission, by an operator to the patient, for example to his terminal MP, of a message asking the patient to consult a doctor. The operator receiving the alarm signal AL1, AL2 may trigger an emergency procedure, and the message transmitted to the terminal MP of the patient may alert the latter that he should consult a doctor urgently. The alarm signals AL1, AL2 may also trigger the displaying of messages on the terminal MP of the patient, before these signals are transmitted to the server SRV. At the end of steps S25 and S26, the processor PRC executes the steps of FIG. 7 again, starting from step S20, in order to acquire and analyze the R-R heart rate again.

FIG. 8 shows steps S30 to S35 of analyzing the QRS complex of an ECG signal. These steps may be executed in step S5 of the procedure P1, if Q and S waves are detected before and after an R wave, respectively. In step S30, the processor PRC analyzes the QRS complex of the ECG signal, in particular in order to determine the duration thereof. In step S31, the processor PRC compares this duration with an upper threshold value QT2. If the duration of the QRS complex is greater than the threshold value QT2, the processor PRC executes step S33, and otherwise the procedure is executed again, starting from step S30, in order to acquire and analyze a new instance of the QRS complex. In step S33, the processor PRC compares the R-R heart rate with a threshold value RT3. For a healthy human, the threshold values QT2 and RT3 are for example set at 120 ms and 500 ms, respectively, corresponding to a heart rate of 120 beats per minute. If the R-R heart rate is greater than the threshold value RT3, the processor executes step S34, and otherwise it executes step S35. In steps S34 and S35, the processor PRC transmits, to the server SRV, the signal SGL and the alarm signals AL1 and AL2, respectively. At the end of steps S34 and S35, the procedure is executed again, starting from step S30.

FIG. 9 shows steps S40 to S46 of analyzing the duration of the PR segment of an ECG signal. These steps may be executed in step S5 of the procedure P1, if P waves are detected before and after an R wave. In step S40, the processor PRC analyzes the PR segment, in particular in order to determine the duration thereof. In step S41, the stability of the duration of the PR segment is analyzed for a certain time, for example between around ten seconds and one minute, while determining whether this duration remains within an interval of for example between −15% and +15% around a mean value. If the duration of the PR segment is stable, the processor PRC executes step S42, otherwise it executes step S46. In step S42, the processor PRC compares the duration of the PR segment with a lower threshold value PRT1. If the duration of the PR segment is greater than the threshold value PRT1, the processor executes step S43, and otherwise it executes step S44. In step S43, if the duration of the PR segment is greater than an upper threshold value PRT2, the processor PRC executes step S45, and otherwise (duration of the PR segment is between the threshold values PRT1 and PRT2) the procedure is executed again, starting from step S40, in order to acquire and analyze a new instance of the PR segment. For a healthy human, the threshold values PRT1 and PRT2 are for example set at 80 ms and 250 ms, respectively. In step S44, the processor PRC compares the R-R heart rate with the threshold value RT2. If the R-R heart rate is greater than the threshold value RT2, the processor executes step S46, and otherwise it executes step S45. In steps S45 and S46, the processor PRC transmits, to the server SRV, the signal SGL and the alarm signal AL1 and the alarm signal AL2, respectively. At the end of steps S45 and S46, the procedure is executed again, starting from step S40.

FIG. 10 shows steps S50 to S54 of analyzing the respiratory rate BR extracted from the signal IS acquired in step S2. These steps may be executed by the processor PRC during step S5 of the procedure P1. In step S50, the respiratory rate is extracted from the impedance signal supplied by the analog circuit AP and the circuit ADC. In step S51, the processor PRC compares the respiratory rate BR with a lower threshold value BRT1. If the respiratory rate BR is lower than the threshold value BRT1, the processor PRC executes step S52, and otherwise it executes step S53. In step S53, the processor PRC compares the respiratory rate BR with an upper threshold value BRT2. If the respiratory rate BR is greater than the threshold value RT2, the processor PRC executes step S54, and otherwise (the respiratory rate is between the threshold values BRT1 and BRT2) it continues to monitor the respiratory rate by executing steps S50 and S51 again. The threshold values BRT1, BRT2 depend on the patient's profile. For a healthy human, the threshold values BRT1, and BRT2 are for example set at 10 and 25 breathing cycles per minute, respectively. In steps S52 and S54, the processor PRC transmits the signal SGL and the alarm signals AL1 and AL2, respectively, to the server SRV. At the end of steps S52 and S54, the procedure is executed again, starting from step S50. In steps S52 and S54, the processor PRC may also transmit the value of the respiratory rate BR.

Each time the processor PRC transmits the alarm signal AL1 or AL2, it may also transmit, to the server SRV, the samples of the signal SGL/IS that led to this alarm signal being transmitted, and also information regarding the nature of the detected anomaly.

Of course, it is possible to implement methods for analyzing an ECG signal other than those described with reference to FIGS. 6 to 10. Thus, there may be provision to compare the signal SGL with a reference signal. The reference signal may be Obtained during an initialization phase of the processing circuit DPR, by triggering the acquisition of an ECG signal from the patient at rest (for example when sitting), and then by triggering the acquisition of an ECG signal from the patient when moving. Each ECG signal may be acquired for a few minutes, for example 2 minutes. Each signal thus acquired is then stored as a reference signal by the processor PRC. The reference signal may also be supplied by the server SRV to the processing circuit DPR. This reference signal may thus be independent of the patient, An example of a reference ECG signal REF is shown in FIG. 11. The processing of a signal SGL acquired by the circuit DPR may comprise a processing operation of comparing the signal SGL with the reference signal REF. To this end, the signal REF is processed in order to extract a certain number of parameters therefrom, such as:

the positions and the amplitudes of the P, Q, R, S and T waves in the signal REF, the positions of the P and Q waves being defined with respect to the position of the following R wave, and the positions of the S and T waves being defined with respect to the preceding R wave, the voltage of the isopotential I of the signal REF (sought for example between −y and −y, y being chosen to be equal to a value between 0.025 and 0.5 mV), the slope of the signal REF between the peaks of the Q and R waves, the slope of the signal REF between the peaks of the R and S waves, the slope of the signal REF between the peak and the end S1 of the S wave, the slope TS1 of the signal REF between the start T0 and the peak of the T wave, the slope TS2 of the signal REF between the peak and the end T1 of the T wave, the slope PS1 of the reference signal between the start P0 and the peak of the P wave, the slope PS2 of the signal REF between the peak and the end P1 of the P wave, the duration between the peaks of the R waves in the signal REF, the voltages yP, yQ, yS and yT of the peaks of the P, Q, S and T waves in the signal REF, and the duration between the peaks of the Q and T waves in the signal REF.

Mean values of these parameters over the duration of acquisition of the reference signal REF may be calculated.

The respective mean positions of the peaks of the P, Q, S and T waves of the reference signal REF make it possible to define reference zones for the peaks of the P, Q, S and T waves of the signal SGL acquired by the circuit DPR. The reference zone for the P wave may be defined between the instants tj−210 ms and tj−80 ms, tj being the instant of the peak of the following R wave, and between the voltages yP+/−x %. The reference zone for the Q wave may be defined between the instants tj−70 ms and 0-50 ms and between the voltages yQ+/−x %. The reference zone for the S wave following the R wave at the instant tj may be defined between the instants tj and tj+80 ms and between the voltages yS+/−x %. The reference zone for the T wave following the R wave at the instant tj may be defined between the instants tj+200 and tj+400 ms and between the voltages yT+/−x %. The quantity x % may be defined between 5 and 15% by an operator. The slopes PS1, PS2, Q-R, R-S, TS1 and TS2 also make it possible to define acceptable reference windows of between 5 and 15% of the respective mean slopes extracted from the reference signal REF. Further parameters may thus be extracted from the reference signal REF, these parameters being used to define reference windows centered on a mean value of one of these parameters. Corresponding parameters are extracted from the acquired signal SGL, and, if they are not located within the corresponding window, an alarm signal AL1/AL2 is generated and transmitted to the server SRV.

The processing operation of comparing the signal SGL acquired by the circuit DPR with the reference signal REF may consist, for the processor PRC, in searching for the peaks of the R waves, for example through a comparison with a threshold voltage (step S3), in determining the value of the voltage of the isopotential I and in determining whether this value is contained within the interval [−y, +y] (y being between 0.025 and 0.5 mV, for example chosen to be equal to 1 mV), in searching for the peaks of the P, Q, S and T waves with respect to the peak of an (or of each) R wave in the signal SGL, and in determining the slopes PS1, PS2, Q-R, R-S, TS1 and TS2 in the signal SGL (step S5), and lastly in determining whether the peaks of the P, Q, S and T waves of the signal SGL are situated within the reference zones defined above on the basis of the reference signal REF, and whether the slopes are situated within the reference windows defined above on the basis of the reference signal REF (step S6). If the R waves are not detected in the signal SGL or if the voltage of the isopotential I is not situated within the interval [−y, −y], or else if the S wave of the signal SGL has an anomaly (peak of the wave outside of the reference zone, or slopes(s) outside of the reference window(s)), the processor PRC transmits the digitized signal SGL in association with the alarm signal AL2 (step S9). If the P, Q or T wave of the signal SGL has an anomaly (peak of the wave outside of the reference zone, or slopes(s) outside of the reference window(s)), the processor PRC transmits the digitized signal SGL in association with the alarm signal AL1 (step S9).

The operators may use the terminal OT to command the updating of the various threshold values, the various dimensions and positions of the reference zones, and the widths of the reference windows described above, which updating is implemented by the processor PRC of the circuit DPR of a designated patient. The operators may also trigger the updating of all or some of the program executed by the processor PRC. Thus, the various threshold and signal values used in the processing operations described above may be modified upon a request transmitted by the server SRV to the processing circuit DPR via the mobile terminal MP of the patient. This provision makes it possible to tailor the detection of the anomalies to the current physiological conditions of each patient. Likewise, the program executed by the processor PRC may be modified and replaced with a new program upon a request transmitted by the server SRV to the processing circuit DPR via the mobile terminal MP.

The server SRV thus receives, from a plurality of processing circuits DPR of patients, alarm signals AL1, AL2 each associated with samples of signals SGL, and also a patient identifier supplied by the dedicated application installed in the terminal MIP or by the processor PRC. These data are decrypted, where necessary, and then stored in the database DB, for example in two tables depending on the alarm level AL1, AL2. Operators are able to view the data stored in the database DB by way of terminals OT connected to the server SRV, in the form of timing charts of the transmitted signals SGL that are reconstructed from the samples of the signal SGL sent by the processor PRC with knowledge of the sampling period (each sample or sequence of samples being time-stamped). The server SRV may trigger the displaying, by a terminal OT, of the signals SGL associated with an alarm signal AL2, in particular when the terminal OT is not already showing such a signal. The signals SGL, associated with an alarm signal AL2 are displayed with priority by the terminals OT, the signals SGL associated with an alarm signal AL1 being displayed when all of the signals SGL associated with an alarm signal AL2 have been processed.

The processing of a signal SGL by an operator may consist in viewing and analyzing the signal SGL in the form of a curve reconstructed from the transmitted signal samples in order detect anomalies therein, and in transmitting a notification to the terminal MP of the corresponding user depending on the anomalies that are found. To this end, the data relating to the user and stored in the database DB may be recovered on the basis of the identifier of the user that is transmitted with the signal SGL data, and displayed on the screen of the terminal OT.

The notifications able to be transmitted upon a command from the operator may comprise a first notification, intended to activate an enhanced monitoring mode in which the signal SGL is systematically transmitted by the circuit DPR to the server SRV via the terminal MP, either in real time or in packets, for example of 12 or 24 hours of signal SGL recordings. A second notification may trigger the displaying, by the terminal MP, of a message intended for the patient, for example advising him to make an appointment with his doctor. A third notification may trigger the displaying, by the terminal MP, of a message intended for the patient, asking him to make an appointment with his doctor as soon as possible. A fourth notification may trigger the display, by the terminal MP, of a message intended for the patient, asking him to go to the emergency department of the nearest hospital or not to move and await the emergency services. To this end, the data transmitted with the alarm signal AL2 comprise the geographical position of the terminal MP. It should be noted that the geographical position of the terminal MP may be transmitted only upon a request received from an operator terminal OT. An operator connected to the server SRV is able to call the emergency services in the vicinity of the geographical position of the patient. The server SRV may also transmit a message relating to the anomaly that is found to the patient's doctor, possibly with the signal SGL portion in which the anomaly has been found. Of course, the enhanced monitoring mode may be activated when one or the other of the second to fourth notifications is sent.

The database DB may thus comprise what is termed a 'hot' database and what is termed a 'cold' database. The hot database stores recent data, transmitted over the last weeks (6 to 12 weeks) by the patients' processing circuits DPR, and in particular identity data, the data transmitted in relation to heart rate continuously recorded each day over several weeks, the anomalies detected and confirmed by an operator in association with the transmitted signals SGL and with a description of the action taken (notification sent) by the operator. The cold database stores, for each patient, medical data, and all of the signals and the alarms associated with the transmitted signals, without a duration limit, and also, in particular, the version of the software installed in the circuit DPR, and/or the values of operating parameters and of anomaly detection parameters implemented by the patient's circuit DPR, such as the various threshold values described above and the various values defining the detection windows for the P, Q, S and T waves implemented by the circuit DPR.

FIG. 12 shows an exemplary embodiment of the hardware architecture of the acquisition system. The acquisition system comprises at least two redundant data centers DC receiving and storing the data of physiological signals and the alarm signals sent by the mobile terminals MP of the patients, at least one monitoring center SC that pools the operator terminals OT having access to the data stored in the data centers DC. The data are transmitted between the terminals MP, the monitoring center SC and the data centers DC by way of one or more networks NT, including the Internet. The data stored in the data centers DC are able to be accessed by terminals MT connected to the network NT, patients' doctors or doctors involved in the medical monitoring service.

The operator terminals OT may be interconnected in a local network linked to the network NT by way of one or more routers or modems MR.

The data centers DC may be linked to the network NT by way of a load-balancing device LB, the processing of a data transmission request sent by the terminals MP or a data sending request requested by the terminals OT, MT being handled each time by the least busy data center DC. Each time one of the data centers DC receives data from a terminal MP by way of the network NT, it transmits said data instantly (with a very small latency of typically less than 5 ms) to the other data center DC by way of a dedicated private link PL. In this way, the data stored by the two data centers are identical.

Each data center DC may comprise a database system that pools all of the data received from the terminals MP, OT, and a plurality of servers SRV organized into clusters and dynamically assigned to processing a data request or data storage request depending on the load of each server. The servers SRV of each data center have access to the database system DB of the data center in order to store the received data and read the data requested by the terminals OT, MT.

It will be clearly apparent to those skilled in the art that the present invention is open to numerous implementation variants and numerous applications. In particular, the invention is not limited to capturing and processing ECG signals, or to the use of electrodes in contact with a patient's skin, in order to acquire physiological signals. The invention is also not limited to the use of an impedance measurement to determine whether electrodes are in contact with a patient's skin. Other methods within the scope of those skilled in the art may easily be implemented. Likewise, means other than a garment, such as glue, may be used to keep electrodes or sensors at a precise location on a patient's skin.

It also goes without saying that the hardware structure of the device for acquiring physiological signals constitutes an invention in its own right that is able to implement monitoring methods other than those defined in the appended claims.

Moreover, the ECG signal processing algorithms described with reference to FIGS. 5 to 11 constitute inventions in their own right, and may thus be implemented independently of the methods, described above, for capturing these signals, and using ECG signal acquisition devices other than those described above.

There may also be provision for the server SRV to apply further processing operations to the signals SGL received from the devices DPR, such as filtering processing operations that make it possible to eliminate more 'false-positive' cases in order to reduce the analytical workload of the operators. Specifically, it may be advantageous for the server SRV, which has higher-performance computing means than the processor PRC, to execute tests for analyzing the signals SGL received from the devices DPR, in order to exclude the signals not indicating any actual anomaly from analysis by an operator, for example by utilizing information in relation to the patient that is available in the database DB. Of course, these processing operations should not increase the risk of occurrence of 'false-negative' cases. If the server SRV detects a case to be processed by an operator in a received signal SGL, the processing operation applied to the signal received by the server SRV may lead to modification of the alarm signal AL1/AL2 transmitted by the device DPR or to the refinement thereof though the introduction of further priority levels.

Moreover, the mobile terminal MP and the processing circuit DPR may be integrated into one and the same signal transceiver and processing unit. To this end, the processing circuit DPR may integrate transmission circuits that use mobile telephony networks.

The invention claimed is:

1. A method for monitoring physiological signals, comprising:
    acquisition of samples of at least one digitized physiological signal, using a device carried by a user,
    detection, by the device, of events in the digitized physiological signal and extraction, by the device, of characteristics of the detected events,
    searching, by the device, for an anomaly in the events and the extracted event characteristics,
    in response to detecting an anomaly, determining a treatment priority level for the detected anomaly, from among two priority levels, the anomalies of a higher priority level being shown before the anomalies of a lower priority level on an operator terminal linked to a server, and
    transmission, via a wireless link in encrypted form, of the digitized physiological signal, by the device, to the server via a mobile terminal when the anomaly is detected or when an enhanced monitoring mode is activated, and otherwise the digitized physiological signal is erased by the device.

2. The method as claimed in claim 1, comprising steps of:
    acquiring a signal of impedance variation between electrodes in contact with the user's skin,
    comparing the impedance variation signal with a threshold value,
    transmitting a notification to the user by way of the mobile terminal so as to inform said user that the electrodes are not in contact with his skin, when the impedance variation signal does not exceed the threshold value, and
    extracting a respiratory rate of the user from the impedance variation signal when the impedance variation signal exceeds the threshold value.

3. The method as claimed in claim 2, comprising steps of comparing the respiratory rate with lower and upper threshold values, and detecting an anomaly if the respiratory rate is not between the lower and upper threshold values.

4. The method as claimed in claim 1, wherein the characteristics of events detected in the digitized physiological signal comprise parameters extracted from the digitized physiological signal, the anomaly being detected if one of the extracted parameters does not belong to a window centered on a mean value of a corresponding parameter extracted from a reference digitized signal.

5. The method as claimed in claim 1, wherein the digitized physiological signal comprises an electrocardiogram signal, the detected events are R, P, Q, S and T waves, and the characteristics extracted from the events relate to the respective amplitudes of these waves and/or to the duration of time intervals between these waves, the R waves being detected in the digitized physiological signal by comparing the electrocardiogram signal with a threshold value, and the P, Q, S and T waves being sought in windows determined on the basis of an instant of detection of an R wave.

6. The method as claimed in claim 5, comprising steps of:
    determining a heart rate by counting the number of R waves per unit of time, the anomaly being detected when the measured heart rate has an instability greater than a first instability threshold value, or when the measured heart rate is not between first and second heart rate threshold values, and/or steps of:
    determining a duration between the Q and S waves, and comparing the duration between the Q and S waves with a threshold value for the duration between the Q and S waves, an anomaly being detected when the duration between the Q and S waves is greater than the threshold value for the duration between the Q and S waves, and/or steps of:
    determining a duration between the P and R waves, comparing an instability of the duration between the P and R waves with a second instability threshold value, comparing the duration between the P and R waves with two threshold values for the duration between the P and R waves, and
    detecting the anomaly when the instability of the duration between the P and R waves is greater than the second instability threshold value or when the duration between the P and R waves is not between the two threshold values for the duration between the P and R waves.

7. The method as claimed in claim 1, wherein the digitized physiological signal comprises an electrocardiogram signal, the detected events are R, P, Q, S and T waves, and the characteristics extracted from the events detected in the digitized physiological signal relate to respective amplitudes of these waves, and/or to a duration of time intervals between these waves, and/or slopes between a peak and a base of these waves, the method comprising steps of:
    acquiring a reference signal,
    determining characteristics of the R, P, Q, S and T waves in the reference signal,
    determining a reference window for each of the characteristics extracted from the R, P, Q, S and T waves of the reference signal, and generating an alarm signal when a characteristic extracted from the digitized physiological signal is not located within a corresponding reference window from among the reference windows determined on the basis of the reference signal.

8. The method as claimed in claim 1, comprising steps of:
detection, by the server, of events in the received digitized physiological signal, and extraction, by the server, of characteristics of the detected events,
searching, by the server, for the anomaly in the events and the extracted event characteristics, and
transmission, by the server, of the received digitized physiological signal to an operator terminal when the anomaly is detected by the server.

9. The method as claimed in claim 1, comprising steps of:
rendering and displaying of the physiological signal by an operator terminal on the basis of the digitized physiological signal received by the server, and
transmission, to the mobile terminal, of a notification sent by the operator terminal and relating to the physiological signal shown on the display screen, and transmission of the notification to the user by way of the mobile terminal.

10. The method as claimed in claim 9, wherein the notifications sent by the operator terminal to the mobile terminal comprise at least one of the following elements:
an order to activate the enhanced monitoring mode that is transmitted from the mobile terminal to the device, the device transmitting the digitized physiological signal upon receipt of the activation order and for as long as the enhanced monitoring mode is activated,
a notification to be transmitted from the mobile terminal to the user so as to inform the user that he should consult his doctor,
a notification to be transmitted from the mobile terminal to the user so as to inform the user that he should await the emergency services or visit a hospital immediately, and
parameters for detecting anomalies in the events and the extracted event characteristics, which parameters are transmitted from the mobile terminal to the device, the device using the received detection parameters to detect anomalies, the detection parameters comprising threshold values and/or reference window widths and/or reference zone dimensions and positions.

11. A device for monitoring physiological signals, configured to be carried by the user and to acquire, in real time, a digitized physiological signal, and transmit the digitized physiological signal to a server via a mobile terminal,
wherein the device is configured to implement the method as claimed in claim 1.

12. The device as claimed in claim 11, comprising electrodes and/or a sensor integrated into a garment, an analog processing circuit connected to the electrodes and/or to the sensor by way of conductive links integrated into the garment, a digital processing circuit connected to the analog processing circuit, and a transceiver circuit connected to the digital processing circuit, the transceiver circuit being configured to communicate with the mobile terminal.

13. The device as claimed in claim 12, wherein the electrodes are placed in the garment so as to come into contact with the user's skin in the region of the shoulder blades or of the sides level with the sternum, the electrodes being formed by printing on the garment, and the conductive links being formed by a conductive wire coated with an insulating layer and inserted into the fabric forming the garment.

14. A system for monitoring physiological signals, comprising:
a server,
a mobile terminal of a user, comprising a communication circuit for establishing communication with the server,
a device carried by the user and configured to acquire, in real time, a digitized physiological signal, and transmit the digitized physiological signal to the server via the mobile terminal,
wherein the system is configured to implement the method as claimed in claim 1.

15. A method for monitoring physiological signals, comprising:
acquisition of samples of at least one digitized physiological signal, using a device carried by a user,
detection, by the device, of events in the digitized physiological signal and extraction, by the device, of characteristics of the detected events,
searching, by the device, for an anomaly in the events and the extracted event characteristics, and
transmission, via a wireless link in encrypted form, of the digitized physiological signal, by the device, to a server via a mobile terminal when an anomaly is detected or when an enhanced monitoring mode is activated, and otherwise the digitized physiological signal is erased by the device,
wherein the digitized physiological signal comprises an electrocardiogram signal, the detected events are R, P, Q, S and T waves, and the characteristics extracted from the events detected in the digitized physiological signal relate to respective amplitudes of these waves, and/or to a duration of time intervals between these waves, and/or slopes between a peak and a base of these waves, the method further comprising:
acquiring a reference signal,
determining characteristics of the R, P, Q, S and T waves in the reference signal,
determining a reference window for each of the characteristics extracted from the R, P, Q, S and T waves of the reference signal, and
generating an alarm signal when a characteristic extracted from the digitized physiological signal is not located within a corresponding reference window from among the reference windows determined on the basis of the reference signal.

* * * * *